(12) United States Patent
Jenne et al.

(10) Patent No.: US 6,861,223 B2
(45) Date of Patent: *Mar. 1, 2005

(54) RIBOZYME-ENCODING DNA AND A COMPOSITION CONTAINING AN OLIGONUCLEOTIDE SUBSTRATE AND A METHOD FOR MEASURING TRANSCRIPTION RATES

(76) Inventors: Andreas Jenne, Angerweg 12, D-89253 Rimsting (DE); Michael Famulok, Leonardusstrasse 26, D-53175 Bonn (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/215,854

(22) Filed: Aug. 8, 2002

(65) Prior Publication Data

US 2003/0008315 A1 Jan. 9, 2003

Related U.S. Application Data

(63) Continuation of application No. 09/646,306, filed as application No. PCT/EP99/01776 on Mar. 17, 1999, now Pat. No. 6,451,535.

(30) Foreign Application Priority Data

Mar. 17, 1998 (DE) .......................... 198 11 618

(51) Int. Cl.[7] .......................... C12Q 1/68; C07H 21/04
(52) U.S. Cl. .......................... 435/6; 536/23.2
(58) Field of Search .......................... 435/6; 536/23.2

(56) References Cited

U.S. PATENT DOCUMENTS

| 5,496,698 | A | * | 3/1996 | Draper et al. | 435/6 |
| 5,719,031 | A | * | 2/1998 | Haugland et al. | 435/7.4 |
| 5,747,338 | A | * | 5/1998 | Giese et al. | 435/348 |
| 6,037,137 | A | * | 3/2000 | Komoriya et al. | 435/23 |
| 6,140,055 | A | * | 10/2000 | Todd et al. | 435/6 |
| 6,214,546 | B1 | * | 4/2001 | Asher et al. | 435/6 |

FOREIGN PATENT DOCUMENTS

| EP | 0 731 178 | * | 9/1996 |
| WO | -96/27026 | * | 9/1996 |
| WO | WO 97/26333 | | 7/1997 |

* cited by examiner

Primary Examiner—Kenneth R. Horlick
(74) Attorney, Agent, or Firm—Birch, Stewart, Koalsch & Birch, LLP (57) ABSTRACT

Compositions (reporter systems), which contain a ribozyme-encoding DNA sequence and an oligonucleotide substrate that is cleaved by the ribozyme transcribed by the DNA sequence, are described. In a preferred embodiment, the oligonucleotide substrate is labeled by a fluorophore group (reporter group) and a fluorescence-quenching group (quencher group), the fluorescence of the fluorophore being prevented from being quenched by the fluorescence-quenching group after cleavage by the ribozyme has taken place, and therefore a fluorescence signal is generated. Moreover, methods for measuring transcription rates, for instance for determining transcription-inhibitors or transcription activators, are described.

14 Claims, 4 Drawing Sheets

RIBOZYME-ENCODING DNA AND A COMPOSITION CONTAINING AN OLIGONUCLEOTIDE SUBSTRATE AND A METHOD FOR MEASURING TRANSCRIPTION RATES

This application is a continuation of U.S. patent application Ser. No. 09/646,306, filed on Nov. 20, 2000 which issued as U.S. Pat. No. 6,451,535, the entire contents of which are hereby incorporated by reference. This application also reclaims priority under 35 U.S.C. §119 to German Application No. 19811618.7, filed in Germany on Mar. 17, 1998 and International Application No. PCT/EP99/01776 filed Mar. 17, 1999.

The present invention relates to compositions (reporter systems) containing a DNA sequence encoding a ribozyme, preferably a hammerhead ribozyme, and a oligonucleotide substrate which is cleaved by the ribozyme transcribed by the DNA sequence. In a preferred embodiment, a FRET oligonucleotide is used, i.e. an oligonucleotide substrate which is labeled with a fluorophore group (reporter group) and a fluorescence-quenching group (quenching group), wherein the fluorescence of the fluorophore is prevented from being quenched by the fluorescence-quenching group after cleavage by the ribozyme has taken place, and therefore a fluorescence signal is generated. Moreover, the present invention relates to methods for measuring transcription rates, for instance for determining transcription inhibitors or transcription activators, with the use of the composition of the invention, and methods for measuring the catalytic activity of ribozymes.

As a rule, the mechanisms of eukaryotic and prokaryotic transcription are examined by methods by which the mRNA is synthesized in vitro (in vitro transcription) in a cell free system, that is to say with the use of correspondingly processed cell extracts. For the production of transcripts, specifically developed transcription vectors which also carry the promoter for a corresponding RNA polymerase in addition to the reporter gene are used in this process. For instance, if the influence of particular transcription activators on the transcription is to be examined, the mRNA of the coding reporter gene must be detectable and quantifiable with suitable methods. For this purpose, radioactively labeled nucleoside triphosphates which are incorporated into the resulting mRNA, are in general added to the cell extract. The radioactively labeled mRNA is then isolated from the cell extract, electrophoretically separated on a polyacrylamide gel and visualized and quantified by autoradiography (T. Maniatis, E. Firsts, J. Sambrook, Molecular cloning: A Laboratory Manual, Cold Spring Harbor Laboratory Press, New York (1982) 6.45). An alternative method, the so-called dot-hybridization technique, uses radioactively labeled RNA probes to detect the in vitro transcribed mRNAs (J. Flores et al., Lancet 1 (1983), 555–558). In principle, there also exists the possibility of detecting transcription indirectly via the activity of the luciferase enzyme, wherein the transcription of the luciferase reporter gene is coupled to an in-vitro translation system. The disadvantages of the above-described and partly routinely used assay methods are in particular the use of larger amounts of radioactively labeled nucleoside triphosphates and/or the high amount of methodical work and time involved in the quantification of the RNA transcripts. More suitable methods for a direct, fast and sensitive measurement of transcription rates are, however, of interest not only for scientific questions, but also for the biotechnological industry. For instance, in the so-called high throughput screening combinatory substance libraries are screened for potential guiding structures which influence the transcription of particular therapeutically relevant target genes. For these and similar applications too, a technically simple, sensitive assay system would constitute a great progress, as there are no satisfactory solutions so far.

Thus, the present invention is based on the problem of providing methods and systems suitable for these methods which permit a simple and sensitive measurement of transcription rates.

This technical problem is solved by the embodiments characterized in the patent claims. It has been found that the composition of the invention (reporter system) surprisingly allows the above-mentioned problems to be circumvented. This system has the following advantages inter alia:

Direct detection of the mRNA in the cell extract.

Fast, reproducible and technically simple quantification of transcription rates, for instance via automated fluorescence measurement.

Highly sensitive and highly specific detection of even the smallest amounts of RNA transcripts (catalytic principle for signal intensification).

Simple control of the course of transcription, for instance by time-dependent fluorescence measurement (real time analytics).

Thus, the present invention relates to a composition containing (a) a ribozyme-encoding DNA sequence which is operatively linked to a promoter and/or regulatory elements; and (b) an oligonucleotide substrate which is cleaved by the ribozyme transcribed by the DNA from (a), with a directly measurable signal being generated after cleavage, as the cleaved oligonucleotide substrate can be distinguished from the non-cleaved oligonucleotide substrate.

The expression "ribozymes" as used herein relates to catalytic RNA molecules capable of cleaving other RNA molecules at phosphodiester bonds in a manner specific to the sequence. Here, the hydrolysis of the target sequence to be cleaved is always initiated by the formation of a catalytically active complex consisting of ribozyme and substrate RNA. After cleavage, the hydrolyzed substrate oligonucleotide dissociates from the ribozyme; the latter is then available for further reactions.

In principle, all ribozymes capable of cleaving phosphodiester bonds in trans, that is to say intramolecularly, are suitable for the purposes of the invention. Apart from ribonuclease P (C. Guerrier-Takada et al., Cell 44 (1983) 849–857) the known naturally occurring ribozymes (hammerhead ribozyme, hairpin ribozyme, hepatitis delta virus ribozyme, Neurospora mitochondrial VS ribozyme, group I and group II introns) are catalysts, which, however, cleave or splice themselves and which act in cis (intramolecularly) (review article in P. Turner (editor), Ribozyme protocols, Humana press (1997), 1–9). By separating the catalytic unit from the sequence containing the cleavage site it was in all cases possible to obtain ribozyme variants cleaving in trans: the hammerhead ribozyme (J. Haselhoff and W. Gerlach, Nature 334 (1988), 585–591); hairpin ribozyme (A. Hampel and R. Tritz, Biochemistry 28 (1989), 4929–4933); the hepatitis delta ribozyme (M. Been, Trends Biochem. Sci. 19 (1994) 251–256): the Neurospora mitochondrial VS ribozyme (H. Guo et al., J. Mol. Biol. 232 (1993) 351–361); the group I intron from tetrahymena (Zaug et al., Nature 324 (1986) 429–433; the group II intron (S. Augustin et al., Nature 34 (1990) 383–386).

The term "promoter" as used herein relates to any DNA sequence by which the transcription of the DNA sequence operatively linked thereto is controlled via the corresponding RNA polymerase in vivo (or in vitro) in prokaryotic or eukaryotic systems. Such promoters are known to a skilled person and for instance include PolII promoters, SP6, T3 and T7 promoters. The endogenous ribozyme expression in eukaryotic cells or cell extracts can, for instance, be carried out by insertion of the ribozyme-encoding DNA sequence into the non-translated region of genes which are transcribed by the RNA polymerase II and are under the control of highly transcribing promoters. Examples include viral promoters, such as the early SV40 promoter (F. Cameron and P. Jennings, Proc. Natl. Acad., Sci., USA 86 (1989) 9139–9143), the promoter of the actin gene (N. Sarver et al., Science 247 (1990) 1222–1225) or a retroviral long terminal repeat, such as HIV-LTA (Koizumi et al., Gene 117 (1992), 179–184).

In a preferred embodiment of the invention, the ribozyme is a hammerhead ribozyme. The hammerhead ribozyme measuring only about 30 nucleotides in length is one of the smallest known ribozymes catalyzing the site-specific hydrolysis of phosphodiester bonds (review article: K. Birikh et al., Eur. J. Biochem. 245 (1997) 1–16). The ribozyme structure comprises three double-stranded areas (helices I, II and III), flanking the cleavable phosphodiester bond, and two highly conserved single-stranded sequences (O. Uhlenbeck, Nature 328 (1987), 596–600). By separating the catalytic core sequence from a sequence containing the cleavage site it was possible to prepare ribozyme variants capable of cleaving nearly any target RNA in trans under physiological conditions (J. Haselhoff and W. Gerlach, Nature 334 (1988), 585–591).

In connection with the very promising therapeutical possibilities of using hammerhead ribozymes, hammerhead ribozymes have recently been successfully optimized in respect of their kinetic properties (high conversion rates), sequence length (minimal motifs) and substrate specificities. Review articles on this topic are for instance Birikh, Eur. J. Biochem. 245 (1997), 1–16; Burke, Nature Biotech. 15 (1997), 414–415 and Eckstein, Lilley (editors) Nucleic Acids and Molecular Biology 10, Springer publishers (1996), 173–329.

In a preferred embodiment, the above-mentioned promoters can be regulated, i.e. they can for instance be activated by transcription activators or inhibited by particular compounds. Genes of eukaryots and prokaryots differ considerably from each other in respect of the organization of the transcription unit (H. lbelgaufts, Gentechnologie von A bis Z, VCH publishers Weinheim (1990), 219–223). The 5'-flanking area of a eukaryotic gene is often termed promoter region, as it contains a number of distinct DNA sequence elements participating in the control of gene expression. They include the TATA box and initiator sequence, inter alia, which together form the core promoter. The basal transcription is essentially regulated by the basic transcription activators of class II (TF II A, B, D, E, F, H and Pol II). In analogy to basal transcription, the term "activated transcription" is used where additional regulatory elements influence transcription. Activation occurs primarily by a binding of transcription activators to so-called "upstream activating sequences " (UAS). Examples of activated transcription are: SP1 which binds to the SP1 binding site, CREB which binds to the CRE element.

As described herein in more detail, the choice of suitable promoters in a suitable test system allows compounds which activate or inhibit transcription to be identified. The choice of the promoter depends on the type of the in vitro-transcription system (for instance yeast, HeLa or fungal cell extracts) and the RNA polymerase used. The herein-described method permits the determination of whether transcription is inhibited or activated in general, or remains unaffected. The mechanism or the principle of the influence exerted by a specific substance of a compound library is the subject matter of the subsequent tests.

Preferably, the DNA sequence encoding the ribozyme is a linearized vector in which transcription can be terminated by cleavage of the template DNA downstream the ribozyme-encoding DNA with the use of a suitable restriction enzyme. Alternatively, the ribozyme-encoding DNA sequence is operatively linked to a termination signal for transcription in in-vivo application. Such termination signals are known to a skilled person. A general prokaryotic stop signal of transcription is a GC-rich region of particular symmetry which is followed by an AT-rich sequence (A. Wu and T. Platt, Proc. Natl. Acad. Sci. 75 (1978), 5442–5446). For the eukaryotic Pol II, too, there are stop signals allowing transcription to be terminated at a defined site.

In another embodiment of the invention, the ribozyme-encoding DNA is inserted optionally together with the other above-discussed sequences, into a vector permitting the inserted DNA to propagate in a suitable host. Vectors suitable for propagation in prokaryotic or eukaryotic systems are for instance pBR322, pNEB193, pUC18, pUC19 (Biolabs, USA) (J. Sampson and O. Uhlenbeck, Proc. Natl. Acad. Sci. USA 85 (1988), 1033–1037).

The above-described ribozymes (preferably hammerhead ribozymes or hammerhead ribozyme variants) can be used as direct reporters for quantifying transcription rates in in-vitro transcription systems. Here, the reporter RNA is endogenously produced, i.e. by transcription of the coding gene, for instance from a suitable transcription vector.

The compositions according to the invention preferably contain stabilized ribozymes, thus ensuring a longer lifetime of the ribozyme, for instance in in-vitro transcription systems. Here, the ribozyme is transcribed together with stabilizing sequences, which imitate the so-called "capping structures", and in this way increase the stability of the RNA to exonuclease degradation (Gene Therapy 4 (1996), 45–54; M. Sioud et al., J. Mol. Biol. 223 (1992), 831–835).

The term "oligonucleotide substrate" as used herein relates to any oligonucleotide, preferably RNA, which can be cleaved by the ribozyme, the cleaved oligonucleotide substrate is distinguishable from the non-cleaved oligonucleotide substrate and a directly measurable signal is produced.

The substrate for instance carries an anchorage group at one of its end, which permits its immobilization on a suitable matrix, and a reporter group at its other end which serves to detect the immobilized (non-cleaved) substrate. If the ribozyme is absent, the substrate remains intact and can be easily detected after its immobilization on the matrix, because the anchorage group continues to be linked to the reporter group. By contrast, if the ribozyme is present, the reporter-specific signal cannot be detected, because the reporter group was separated from the anchorage group as a result of the cleavage of the substrate. As an alternative to the anchorage group (e.g. biotin), complementary sequence hybridization can also be used to immobilize the substrate, if the cleavage site and reporter group lie beyond the hybridization site. Easily detectable reporter groups which can be easily coupled to nucleic acid ends are for instance $^{32}P$, dye molecules and molecules which can be detected with labeled antibodies.

The oligonucleotide substrate of the invention is essentially complementary to the sequence(s) of the ribozyme which is/are responsible for substrate bonding, i.e. it possesses a complementarity which permits an annealing to the ribozyme in such a way that an effective and specific cleavage of the oligonucleotide substrate is ensured. The oligonucleotide substrate is preferably fully complementary to the ribozyme sequences responsible for substrate binding. The length of the region of the oligonucleotide substrate annealing to the ribozyme amounts to preferably 5 to 8 nucleotides (P. Turner, editors, Ribozyme protocols, Humana press (1997), 151–159, 253–264). At its 5' and/or 3' end, the oligonucleotide substrate can contain additional sequences which do not participate in the annealing to the ribozyme. In a preferred embodiment, the above-mentioned oligonucleotide substrate is double labeled, and the cleaved substrate is easily distinguishable from the intact substrate.

In addition to the ribozyme-encoding DNA, the in-vitro transcription batch for instance contains a terminally biotinylated substrate oligonucleotide, the other end of which is labeled with fluorescein. After a minimum incubation time, sufficient for cleaving the substrate in the case of unhampered transcription, transcription is stopped. The transcription batch is subsequently incubated with a streptavidin-coated solid phase (for instance with a commercially available microtiter plate) in order to enable the biotinylated substrate end to couple to the streptavidin matrix. After removal of the transcription batch and washing of the matrix, the latter is measured. In the case of undisturbed (i.e. non-inhibited) transcription, no fluorescein-specific fluorescence or only a weak unspecific background fluorescence is measurable, as the fluorescein-labeled fragment could not be immobilized. By contrast, if none or only a reduced transcription of the ribozyme occurs, for instance because of inhibition by a transcription inhibitor, the portion of the non-cleaved immobilized substrate can be quantified by measurement of the fluorescein-specific fluorescence.

A method for performing a time-dependent kinetic analysis of ribozymes within hours is provided by the use of FRET oligonucleotides (K. J. Livak, S. J. A. Flood, J. Marmaro, W. Giusti, K. Deetz, PCR Meth. Appln. (1995), 4, 357–362) (FRET=Fluorescence Resonance Energy Transfer) (J. R. Lakowicz, Principles of Fluorescent Spectroscopy; Plenum Press, New York (1983)).

RNA oligonucleotides or DNA-RNA hybrids wherein a fluorophore group (e.g. FAM=6-carboxy-fluorescein, TET=tetrachloro-6-carboxy-fluorescein or HEX=hexachloro-6-carboxy-fluorescein) and a corresponding fluorescence-quenching group, a so-called "quencher" (e.g. sulforhodamine 101 or TAMRA=6-carboxytetramethylrhodamine) are so arranged in spatial proximity that the fluorescence of the fluorophore is effectively quenched are particularly preferred as FRET substrates (Lakowicz, Principles of Fluorescence Spectroscopy, Plenum Press, New York (1983), 303–339; V. Förster, Annals of Physics (Leipzig) 2 (1948), 55–75). After cleavage of the substrate by ribozyme-catalyzed hydrolysis of a particular phosphodiester bond, the fragments can drift apart in solution: The fluorescence of the fluorophore is now no longer intramolecularly quenched. Hence, if the transcription of the reporter ribozyme takes place in the presence of such double labeled substrates, the transcription rate can be quantified via the amount of ribozyme (=mRNA of the reporter gene), because a measurable fluorescence signal is generated at the cleavage of the substrate. Under suitable conditions (for instance excess of substrate) the unquenched fluorescence is proportional to the amount of transcribed reporter ribozyme and the incubation time, and can be quantified via suitable automated read-out device.

Figure 1:
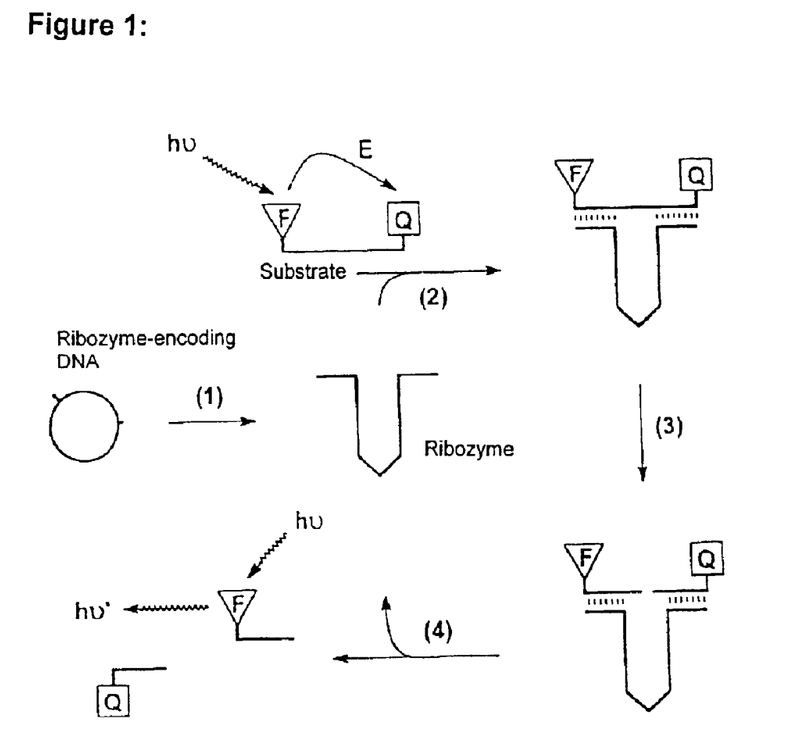
Figure 2:
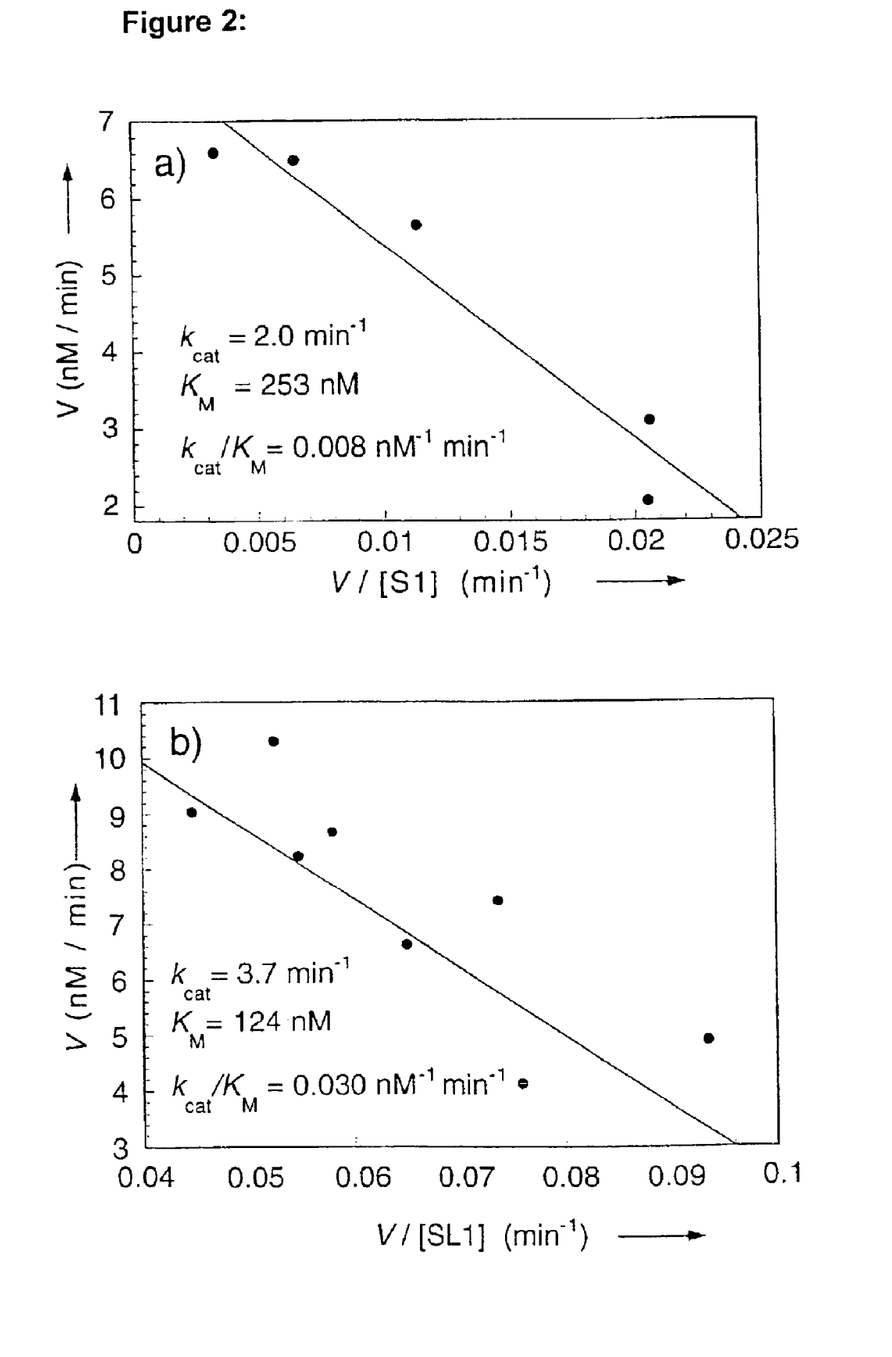

As the increase in fluorescence is directly correlated to the cleavage rate, the system is suitable for a sensitive, non-radioactive and fast analysis of ribozyme activities. A FRET substrate (SL1) was constructed on the basis of a known HHR/substrate complex (M. Fedor, O. C. Uhlenbeck, Proc. Natl. Acad. Sci. USA (1990), 87, 1668–1672) and was used for a time-dependent measurement of ribozyme activity (HHR1). An inactive HHR mutant (HHR1mut) with identical substrate binding sites was used as a reference and negative control. The Michaelis-Menten parameter of HHR can be obtained in a single experiment by measurement of the cleavage-caused rise in fluorescence at different substrate concentrations. FIG. 2b shows the Eadie-Hofstee plot for determining the $K_{cat}/K_M$ values as the result of this measurement.

In order to determine the influence of the FAM/TAMRA labeling on the cleavage efficiency, the kinetic parameters were determined in a conventional manner with a $32_P$ labeled substrate without FRET labeling (S1) (FIG. 2a). The conventional method includes the separation of cleavage products by polyacrylamide gel electrophoresis and the subsequent evaluation of the gels by autoradiography (P. Hendry, M. J. McCall, T. J. Lockett, Characterizing ribozyme cleavage reactions; P. C. Turner (editors); Humana Press: Totowa, N.J. (1997), vol. 74, 221–229).

Both the $K_{cat}$ and the $K_M$ values were found to be in the same order of magnitude for both substrates (S1, SL1), which shows that the FRET substrate is very suitable for the purpose pursued.

In order to find out whether the method is suitable for the fast characterization of ribozymes, the activity was measured in parallel batches while various physico-chemical parameters were modified.

Figure 3:
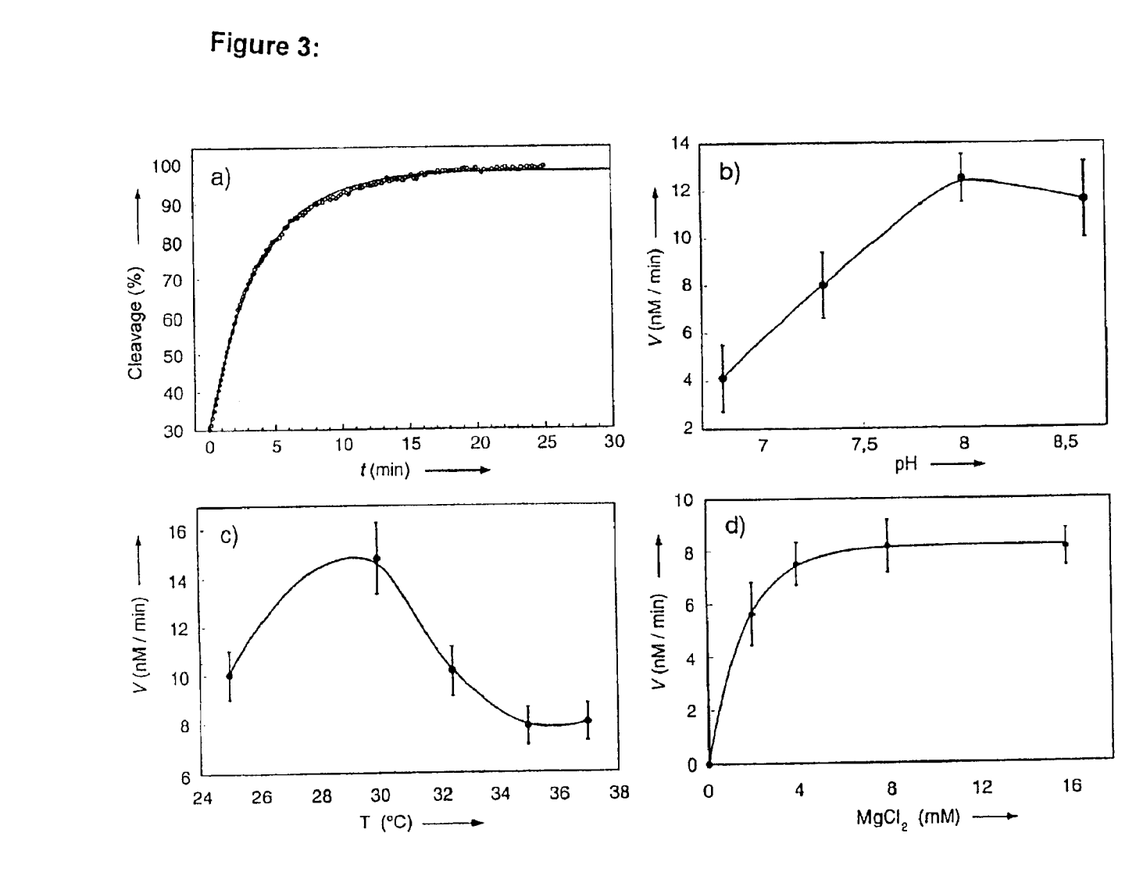

FIG. 3a shows the time-dependent course of cleavage as a result of a typical measurement. FIGS. 3b–d show the dependency of the reaction rate on the pH value, the temperature and the $Mg^{2+}$ concentration. Under the conditions chosen here, a pH optimum was determined at a value of 8, the optimum of $[Mg^{2+}]$ was achieved at 8 mM. The relatively low temperature optimum of 32° C., presumably reflects the relatively weak binding of the substrate to the ribozyme. The latter could be attributable to the short hybridization regions containing only five G-C base pairs with a simultaneously relatively low $Mg^{2+}$ concentration (4.0 mM).

In order to eliminate measurement inaccuracies caused by the equipment or unspecific fluorescence effects (e.g. fluctuation of the signal on account of temperature variations), the data points obtained were corrected by the ribozyme-independent reference values obtained with the inactive mutant HHR1mut. Moreover, the correction procedure also enabled the determination of the activity of ribozymes produced in situ in the presence of cell nucleus extracts.

Figure 4:
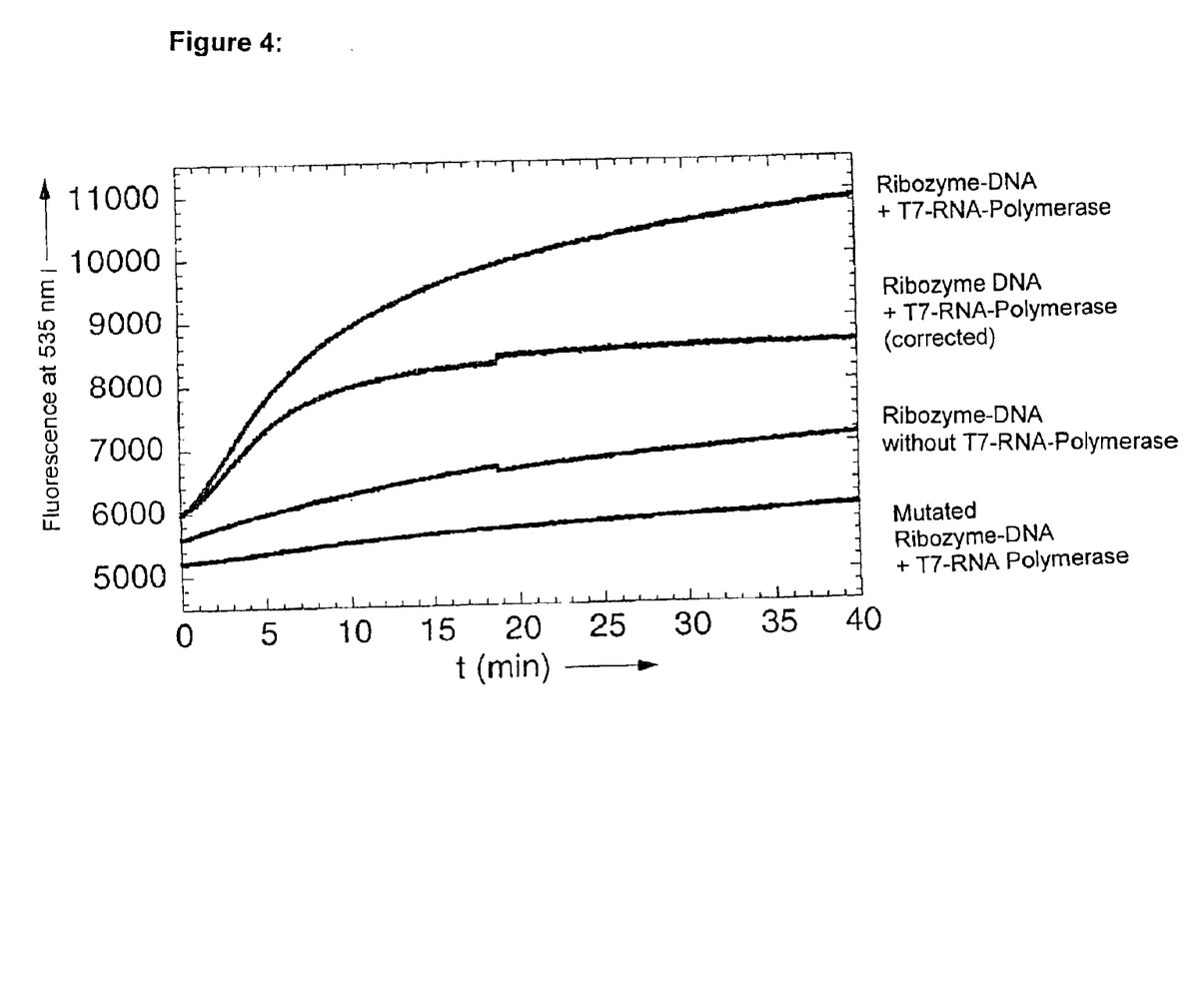

FIG. 4 shows the measurement results of a T7 RNA polymerase dependent transcription of ribozyme-encoding DNA templates in the presence of HeLa cell nucleus extracts. As a control, parallel measurements were made on the one hand in the absence of the T7RNA polymerase, and on the other with the inactive HHR mutant. Both curves show a slight rise in the fluorescence, which is presumably attributable to an unspecific cleavage of the substrate by nucleases in the cell extract. Another curve describes the absolute fluorescence obtained in the measurement in in-situ HHR1-production. Still another curve shows the same measurement corrected by the superimposing background reactions (see example 2).

As expected, the corrected curve shows a sigmoidal course reflecting the steady increase in the ribozyme concentration in the course of the transcription reaction. These results show-that it is in principle possible to use the ribozymes as reporters for measuring transcription rates in vitro and in vivo. Such a reporter system can for instance be used for high throughput screening of combinatory substance libraries for inhibitors of transcription factors, because it can be used in a fully automated way and without additional pipetting steps.

DNA oligonucleotides analogous to the above-described RNA oligonucleotide substrates are commercially available (e.g. from PE Applied Biosystems, Foster City, Calif. USA) or are accessible by a simple synthesis (Livak et al., PCR Methods Appl. 4 (1995) 1–6 and Rudert et al., BioTechniques 22 (1997) 1140–1145). For instance, the double labeled DNA oligonucleotides are used for the semiquantitative analysis of PCR-amplified DNA (Taqman®, PE Applied Biosystems, Foster City, Calif. USA; see for instance also Lang et al., J. Immun. Methods 203 (1997), 181–192). The Taqman®-PCR technique utilizes the intrinsic 5'→3' nuclease activity of the Taq polymerase enzyme: During amplification, the 5' and 3' double labeled DNA oligonucleotide is hydrolyzed by the enzyme. After cleavage of the DNA probe, the fluorophore and the quencher diffuse divergently, resulting in the elimination of fluorescence quenching. Subsequently, the fluorescence of the fluorophore is measured and serves as a yardstick for the amplification achieved (Livak et al., Research News (1995), PA Applied Biosystems, Foster City, Calif., USA).

Similarly to the above-described application of double labeled DNA oligonucleotides, the use of corresponding RNA-based substrates can be realized without any problems. Methods for labeling ribonucleic acids with fluorophore or fluorescence-quenching groups and techniques for measuring the energy transfer (quenching) have already been described in detail (Turner (editors), Ribozyme protocols, Humana press (1997), 241–251). The synthetic and enzymatic preparation of ribozymes and the preparation of linearized transcription vectors are also known to a skilled person (Turner (editors), Ribozyme protocols, Humana press (1997) 51–111). 5'-fluorophore- and 3'-quencher-labeled RNA oligonucleotides are commercially available just as the analogous DNA oligonucleotides (e.g. 5'-FAM and 3'-TAMRA labeled RNA from Eurogentec, Belgium). Labeling is advantageously performed at the RNA ends in order not to exert any influence on the hybridization of the ribozyme.

In order to avoid fluorescence emission accompanied by undesired cleavage (for instance by nucleases in the transcription system), the use of nuclease-resistant oligonucleotide substrates is particularly advantageous (Eaton and Pieken, Annu. Rev. Biochem. 64 (1995), 837–863 and Shimayama et al., Nucleic Acids Res. 21 (1993), 2605–2611). This is particularly advantageous in view of in-vivo applications where the double labeled substrate is exogenously introduced by suitable techniques (for instance microinjection, liposome transport, etc.) into cells (P. Turner (editors), Ribozyme protocols, Humana press (1997), 417–451). Thus, in a particularly preferred embodiment, the double labeled substrates are modified RNA oligonucleotides. As long as the cleavage site in the substrate is NUH↓ (according to the IUB code: N=any base, H=A, U or C), the substrate can contain desoxyribonucleotides or/and modified bases or/and 2'-modified ribose units. In this way, the stability of the substrate in the cell extract is increased (N. Taylor et al., Nucleic Acids Res. 20 (1992), 4559–4565).

Also, the use of internally labeled, instead of terminally labeled oligonucleotide substrates can contribute to an improved signal-noise ratio, as fluorescence-quenching is increased inter alia by shorter intervals between the two groups (fluorophore and quencher).

The present invention also relates to a method for the quantitative determination of transcription rates, which comprises the following steps:

(a) contacting the above-described composition with an in-vitro transcription system under conditions at which the transcription of the DNA sequence encoding the ribozyme occurs and at which the ribozyme is catalytically active; and (b) measurement of the amount of cleaved oligonucleotide substrate after and/or for a suitable period of time.

Hereinafter, the basic procedure to utilize the invention as a simple screening method for identifying transcription inhibitors from combinatory substance libraries is described.

(a) Selection and preparation of the ribozyme-encoding DNA and the double labeled oligonucleotide substrate.

Ribozyme-encoding DNA sequences are known to a skilled person. Depending on the desired ribozyme type and the matching oligonucleotide substrate sequence, the DNA sequence encoding the ribozyme of the invention can be prepared according to techniques known to a skilled person.

Here, either a double-stranded PCR-DNA or a linearized vector serves as a template for the in-vitro transcription of the ribozyme. Methods for preparing corresponding templates are known to a skilled person (Turner (editors), Ribozyme protocols, Humana press (1997), 69–78 and 121–138).

Hammerhead ribozymes are particularly preferred. As the pH, temperature, $Mg^{2+}$ concentration and the type and length of the substrate binding sequences greatly influence the ribosome activity, it is necessary to select that combination of ribozyme and substrate which leads to optimized conversion rates under the physiological conditions of the respective test system. Suitable procedures are known to a skilled person.

A hammerhead ribozyme possessing good intermolecular cleavage properties in respect of the complexed substrate RNA ($K_{cat}/K_m$=0.032 $nM^{-1}$ $min^{-1}$ at pH 7.5, 10 mM $MgCl_2$, 25° C.) is described in Fedor and O. Uhlenbeck, Proc. Natl. Acad. Sci. USA 87 (1990); 1668–1672: 5'-GGG UCC UCU GAU GAG GGC CGU UAG GCC GAA ACU CC-3' (ribozyme) and 5'-GGG AGU CAG GAU-3' (substrate). For instance, advantageous hammerhead ribozyme variants and corresponding substrates can be designed on the basis of these sequences (see example 1). In the design of the ribozyme, attention should be paid not only to the kinetic parameters but also to the fact that apart from the very promoter sequence the transcribed region (of up to 10 nucleotides) directly following the promoter often has a decisive influence on the transcription rates. As the 5'-transcribed sequence is, as a rule, identical with a part of the substrate hybridization region, special care should be taken in the design of the ribozyme and substrate sequences to ensure that both optimal transcription and ribozyme substrate hybridization are enabled. Moreover, in the choice of the double labeled substrate sequence the following points must in particular be borne in mind:

The NUH cleavage (restriction) site is advantageously GUC or AUC.

The emission spectrum of the fluorophore overlaps with the absorption spectrum of the quencher dye.

The substrate should not form intramolecular secondary structures, where possible.

The 5'-terminal base should not be guanosine.

Advantageously, the substrate should symmetrically hybridize to the ribozyme over 12 to at the most 16 nucleotides.

(b) The preparation of the in-vitro-transcription system.

The preparation of cell extracts which are used as in-vitro transcription systems is known to a skilled person. It is also known to a skilled person that in-vitro transcriptions can be carried out in these cell extracts. An example of a suitable in-vitro transcription system is the class II system of human cell nucleus extracts (Matsui et al., J. Biol. Chem. 255 (1980), 11992–11996; and Roeder, Trends Biochem. Sci. 21 (1996), 327–335). Under physiological conditions, the activity of hammerhead ribozymes is, as a rule, high enough, but can be increased for instance by an increase in the $Mg^{2+}$ concentration to 5 to 10 mM. As a rule, this has no influence on transcription.

(c) Carrying out the reaction.

A suitable DNA template enabling the transcription of the desired ribozyme is added to the cell extract. Advantageously, an excess amount of the oligonucleotide substrate is added to the batch, in order to ensure linear, reproducible dependencies between the accumulated reporter ribozyme and the signal measured (preferably a fluorescence signal) during the period of measurement. A parallel measurement of different transcription batches can be made for instance in commercially available 96-well microtiter plates. After addition of the potential inhibitors or activators to be tested, the in-vitro transcription is then started for instance by the addition of the corresponding RNA polymerase. Suitable reaction times are within the range of about 1 minute to about 60 minutes.

The transcription rate is measured by the determination of the fluorescence coupled to the amount of cleaved oligonucleotide substrate. The actual amount of transcribed RNA can be determined in correspondingly calibrated systems. Calibration can be made in the following manner: Known amounts of ribozyme-encoded DNA are incubated with known amounts of double labeled substrate. Here, transcription takes place in the presence of $^{32}P$-$\alpha$-UTP which is incorporated into the ribozyme RNA formed. The rise in fluorescence is then measured time-dependently in identical batches, with the individual batches being stopped at different times. For a quantification of the resulting ribozyme amounts, the batches are separated on a denaturating polyacrylamide gel and evaluated by means of a phosphorus imager. The amount of ribozyme can then be determined for each measurement point via the rate of radio nucleotide incorporation. Finally, the calibration curve for the subsequent measurements is obtained by plotting the relative fluorescence measured against the ribozyme concentration measured.

(d) Measurement of transcription rates and evaluation.

If oligonucleotide substrates labeled with a fluorophore group and a fluorescence quenching group are used, the emitted fluorescence is advantageously measured in an automated manner by means of a suitable read-out device (for instance ABI Prism 770 Sequence Detection System, Perkin Elmer). Calibration methods and methods for measuring the very fluorescence have been described in detail as have programs for computer-aided data processing (textbook on ABI Prism 770 Sequence Detection System, Perkin Elmer; Rudert et al., BioTechniques 22 (1997) 1140–1145). In principle, the fluorescence of the fluorophore is recorded for each transcription batch time-dependently above the background ($\Delta R_n$ value). The evaluation can be carried out subsequently at the very ABI Prism 7700 device, by comparing the spectra of the different batches at different times with the spectrum of the uninhibited reference.

Moreover, the present invention relates to a method for identifying transcription-inhibitors or transcription activators, which comprises the following steps:

(a) contacting the above-described composition with a first in-vitro transcription system and a second transcription system containing the compound to be tested, under conditions at which the transcription of the DNA sequence encoding the ribozyme occurs and at which the ribozyme is catalytically active; and (b) measuring the amount of cleaved oligonucleotide substrate after and/or for a suitable period of time in both transcription systems, with a higher transcription rate in the second transcription system suggesting the presence of a transcription activator and a reduced transcription rate suggesting the presence of a transcription inhibitor.

The basic procedure is identical to the above-described procedure, with the exception that not only one test system is used but two, which only differ in one point, i.e. in that the second test system contains the compound to be tested.

After evaluation of the data, the effect of the addition of the substance on the transcription rate relative to the reference (= uninhibited transcription) can be determined: A lower fluorescence signal suggests inhibition, a higher signal suggests the presence of a transcription activator.

In order to further increase the utility of the above-described ribozymes and the sensitivity of the above-described method, it is possible to apply "in-vitro selection" (Pan, Curr. Op. Chem. Biol. 1 (1997), 17–25; Breaker, Chem. Rev. 97 (1997), 371–390) and ribozyyme engineering techniques (Turner (editors), Ribozyme protocols, Humana press (1997) 11–15, 141–159, 253–273). This allows particularly effective de novo ribozymes or variants of natural ribozymes to be prepared, in order to achieve optimum conversion rates with the non-natural oligonucleotide substrate under the corresponding conditions of the in-vitro transcription system (S. Santoro and G. Joyce, Proc. Natl. Acad. Sci. USA 94 (1997), 4262–4266).

This in-vitro selection has recently been successfully used to produce ribozymes possessing modified substrate specificities and activities (Vaish, Biochemistry 36 (1997), 6495–6501, and Berzal-Herranz et al., Gene Dev. 6 (1992), 129–134). In this connection, the in-trans selection of ribozymes is a particularly advantageous method, with a direct selection for cleavage of the double labeled oligonucleotide substrate (Ishizaka, Biochem. Biophys. Research Com. 214 (1995), 403–409). From the ribozyme sequences obtainable by this method, those ribozymes which show the desired property in the automated fluorescence screening of the cell extracts can be directly selected.

Hence, the present invention also relates to the above-described composition which contains a DNA sequence encoding an in-vitro-selected ribozyme.

Moreover, the present invention relates to the use of the above-described composition for absolute or comparative measurement of transcription rates, preferably by means of the above-described method.

Moreover, the invention relates to the use of the method of the invention for measuring the catalytic activity of ribozymes.

Finally, the present invention relates to kits containing the above-described compositions, preferably for carrying out the method of the invention. Kits, also containing an in-vitro transcription system, for instance one of the above-described systems are preferred according to the invention.

DESCRIPTION OF THE FIGURES

FIG. 1:

A schematic representation of the composition of the invention (in-vitro reporter system). (1) Production of the ribozyme by in-vitro-transcription in the cell extract. A corresponding DNA sequence, for instance deriving from a vector, serves as a template. (2) The binding of the double labeled substrate (for instance 5'-FAM and 3'-TAMRA labeled RNA) to the ribozyme leads to the formation of the catalytically active complex. The fluorescence is intramolecularly quenched in the substrate. (3) Cleavage of the double labeled substrate. (4) Dissociation of the reaction products from the ribozyme. A fluorescence signal hv is measured on account of the elimination of the quenching effect.

FIG. 2:

Determination of the kinetic parameters of HHR1 [4 nM] at 37° C. (a) Eadie-Hofstee plot and kinetic parameters of the cleavage activity of HHR1 with a 5'-$^{32}$P-labeled substrate (S1) not carrying any FRET labeling. (b) Eadie Hofstee plot and kinetic parameters of the cleavage activity of HHR1 with the FRET substrate (SL1).

FIG. 3:

Characterization of the cleavage activity at 4 nM HHR1 and 200 or 300 nM SL1. (a) Time-dependent course of cleavage with the reciprocally exponential regression curve (only 1% of all data points measured are depicted). (b–d) dependence of the reaction rate of the HHR1 on (b) the pH, (c) the temperature and (d) the $Mg^{2+}$ concentration. The $K_{cat}/K_M$ values at 25° C. (0.0134 $nM^{-1}$ $min^{-1}$) were also determined.

FIG. 4:

Time-dependent rise in fluorescence of in-situ-produced HHR and control batches in the presence of HeLa cell extracts. HHR1mut-DNA+T7RNA polymerase, HHR1-DNA without T7 RNA polymerase, HHR1-DNA+T7RNA polymerase, HHR1-DNA+T7 RNA polymerase corrected by the unspecific background activities (see example 2).

The following examples explain the invention.

EXAMPLE 1

Measurement of the Influence of Inhibitors on the in-vitro Transcription with T7-RNA Polymerase 1. Production of the Ribozyme-encoding Template DNA and the 5'-FAM- and 3'-TAMRA-labeled Substrate RNA The ribozyme-encoding DNA sequence HHR1-DNA described in this example and the RNA substrate SL1 are derived from a known hammerhead ribozyme substrate complex (M. Fedor and O. Uhlenbeck, Proc. Natl. Acad. Sci. USA 87 (1990), 1668–1672). The template for the in-vitro transcription of the ribozyme HHR1, the ribozyme-encoding double-stranded HHR1-DNA was produced by polymerase chain reaction (PCR). For this purpose, the sense strand of the ribozyme, including the 5'-terminal T7-promoter sequence, was synthesized with an Expedite Oligonucleotide Synthesizer (Millipore, USA): 5'-TCT AAT ACG ACT CAC TAT A GGG TCC TCT GAT GAG GCC GTT AGG CCG AAA CTC GT-3' (HHR1-DNA; the primer binding sites are written in italics). The synthesis of the antisense strand and the amplification of the double stranded template were carried out with the use of the following primers: 5'-TCT AAT ACG ACT CAC TAT A-3' (5' primer) and 3'-GG CAA TCC GGC TTT GAG CA-5' (3' primer). A typical 100 µl reaction contained 10 mM tris-HCl, pH 8.9, 100 mM KCl, 1.5 mM $MgCl_2$, 50 mg/ml bovine serum albumin, 0.05% Tween 20 (v/v), 200 µM dA/dC/dG/dTTP, 2 µM of 5' and 3' primers, about 200 nM of single-stranded DNA template and 2.5 units of Tth DNA polymerase. Amplification was carried out according to the manufacturer's protocol (Boehringer Mannheim, Tth-DNA polymerase kit) in four to five PCR cycles a 95° C., 55 seconds; 55° C., 1 minute; 72° C., 1 minute. The amplified DNA was subsequently isolated according to standard methods and purified from excess primers by means of agarose gel (T. Maniatis, E. Fritsch, J. Sambrook, Molecular cloning; a Laboratory Manual, Cold Spring Harbor Laboratory Press, New York (1982), 14.2–14.35). Analogously, a double-stranded DNA template encoding an inactive ribozyme variant HHR1mut was prepared starting from the following single-stranded DNA: 5'-TCT AAT ACG ACT CAC TAT A GGG TCC TCT TAG GAG GCC GTT AGG CCA GAA CTC GT-3' (HHR1mut; primer binding sites are written in italics, mutations are emphasized). The following primers 5'-TCT AAT ACG ACT CAC TAT A-3' (5'-primer) and 3'-GG CAA TCC GGT CTT GAG CA-5'-primer) were used.

The 5'-FAM and 3'-TAMRA labeled substrate RNA SL1 having the sequence 5'-FAM-ACG AGU CAG GAU U-TAMRA-3' was purchased from Eurogentec (Belgium) and purified by means of a 20% denaturated polyacrylamide gel (P. Turner (editors), Ribozyme protocols, Humana press (1997) 79–81).

2. In vitro Transcription

A typical 50 µl reaction batch contained: 40 mM tris HCl, pH 8.0, 50 mM NaCl, 2 mM spermidin, 5 mM dithiothreitol, 5 to 25 mM $MgCl_2$, about 500 nM SL1, 0.2 to 2 µM HHR1-DNA or HHR1mut-DNA, 4mM A/C/G/UTP and 50 units of T7-RNA-polymerase. It is important to ensure that only double-stranded DNA is used in transcription, as both single-stranded sense-strand DNA and 3'-primer DNA can inhibit the cleavage reaction. In-vitro transcription was started by the addition of the polymerase, and incubation was carried out at 37° C. while the measurement was taken.

3. Real Time Measurement of Fluorescence at Cleavage of SL1 by HHR1:

The fluorescence of the transcription batches was measured in an automated manner in an ABI Prism 770 spectrometer (Applied Biosystems, USA), the temperature of which could be adjusted. The spectra in the emission wavelength range of the two dyes (FAM, $\lambda_{max}$=518 nm and TAMRA, $\lambda_{max}$=582 nm) were recorded in intervals of 7 seconds (excitation energy=488 nm). After an incubation time of 3 hours, the collected data were evaluated by the software contained in the equipment. For a real time control of the individual transcriptions, the fluorescence spectra (range of 500 nm to 660 nm) were projected time-dependently over the spectrum of the reference transcription (with non-functional HHR1mut DNA). Under optimum transcription conditions a distinct increase in the FAM specific fluorescence could be seen in batches with HHR1-DNA relative to the constant fluorescence of the reference transcription with HHR1mut-DNA. Subsequently, the portion of cleaved substrate RNA relative to the negative control (identical batch with inactive HHR1mut-DNA instead of HHR1-DNA) was determined by plotting the relative fluorescence of the fluorophore ($\Delta R_n$ value) at 535 nm versus time. Methods for calibrating the equipment and programs for computer-aided data processing have been described in detail (textbook on ABI Prism 770 Sequence Detection System, Perkin Elmer; W. Rudert et al., BioTechniques 22 (1997) 1140–1145). As expected, the evaluation of the measurement data for a substrate concentration of 900 nM SL1 showed that the relative fluorescence $\Delta R_n$ of the fluorophore at a constant concentration of HHR1-DNA increased with the incubation times. The inactivated ribozyme HHR1mut had no influence on the fluorescence signal measured.

4. Real Time Measurement of the T7 Transcription Rates in the Presence of T7-RNA Polymerase Inhibitors:

The measurements were carried out in a manner analogous to that under 3., however with T7-lysozyme, an inhibitor of T7-RNA-polmyerase (R. Ikeda, P. Bailey, J. Biol. Chem. 267 (1992), 20153–20159). As expected, $\Delta R_n$ decreased relative to the non-inhibited transcription with an increasing inhibitor concentration.

EXAMPLE 2

Determination of the Activity of in-situ-produced Ribozymes in the Presence of Cell Nucleus Extracts 1. Preparation of the substrate RNA The preparation was carried out as described in Example 1.1.

2. Measurement of the ribozyme activity

A typical 50 µl reaction batch for the in-vitro transcription for the ribozyme production contained 40 mM tris HCl, pH 8.0, 50 mM NaCl, 2 mM spermidin, 5 mM dithiotreitol, 8 mM $MgCl_2$, 0.2–2 µM HHR1-DNA or HHR1mut-DNA, 4 mM A/C/G/UTP, 40 units of RNAsin (Promega, Madison, Wis.) and 50 units of T7 RNA polymerase (Stratagene, Heidelberg). The RNA was purified by means of a 16% denaturing polyacrylamide gel (37.5:1). For the measurement of the ribozyme activity of in-situ-produced HHR1 the batch additionally contained 100 nM SL1 and 10 units of HeLa nucleus extract (HeLa Cell Extract Transcription System, Promega, Madison, Wis.). The in-vitro transcription was started by the addition of the polymerase and nucleus extract and incubation was carried out at 37° C. while the measurement was taken.

The real time measurements of the rise in fluorescence caused by the ribozyme were taken in 50 µl reaction batches. The signal measured comprises both the chemical step of cleavage and the release of the cleavage products. The fluorescence of the transcription batches was measured in an automated manner in an ABI Prism 770 spectrometer (Applied Biosystems, USA), the temperature of which could be adjusted. At intervals of 0.5–0.7 s the spectra in the emission wavelength range of the two dyes (FAM, $\lambda_{max}$=535 nm and TAMRA, $\lambda_{max}$=582 nm) were recorded (excitation energy=488 nm). All measurements were triplet determinations. Subsequently, the portion of cleaved substrate RNA relative to the negative control (identical batch with inactive HHR1mut-DNA instead of HHR1-DNA) was determined by plotting the relative fluorescence of the fluorophore ($\Delta R_n$ value) at 535 nm versus time. The rough data were imported into Microsoft Excel, processed, and subsequently evaluated by means of the program KaleidaGraph (Abelbeck Software, Munich).

In order to eliminate unspecific fluorescence effects of the measurement it was necessary to take into account that at a rise in fluorescence through catalytic cleavage the absolute fluorescence variations increase, while their percentage variations do not. The course of cleavage from an aspect of time was corrected on the basis of the curve measured for the negative controls and their percentage deviation from the initial value from an aspect of time was corrected in accordance with the equation (1):

[$F_{korr}(t)$: corrected fluorescence at time t; $F_{neg}(t)$: fluorescence of the negative control at time t; $F_{neg}(t_o)$: fluorescence of the negative control at time t=0; $F_{HHR}(t)$: rise in fluorescence measured in the presence of transcribed HHR at time t].

What is claimed is:

1. A reporter system comprising:
   (a) a first oligonucleotide which is a ribozyme; and
   (b) a second oligonucleotide which is a substrate oligonucleotide for the ribozyme, said second oligonucleotide comprising a label capable of generating a directly measurable signal only when said second oligonucleotide substrate is cleaved by said ribozyme.

2. The reporter system according to claim 1, wherein the first oligonucleotide is a hammerhead ribozyyme.

3. The reporter system according to claim 1 or 2, wherein the first oligonucleotide and the second oligonucleotide are resistant to nuclease.

4. The reporter system according to claim 1 or 2, wherein the second oligonucleotide is a double labeled oligonucleotide substrate.

5. The reporter system according to claim 4, wherein the double labeled oligonucleotide substrate contains a fluorophore group and a fluorescence-quenching group and wherein after cleavage of said second oligonucleotide by the ribozyme the fluorescence of the fluorophore is not quenched by the fluorescence-quenching group.

6. The reporter system according to claim 5, wherein the fluorophore group is 6-carboxy-fluorescein (FAM) and the fluorescence-quenching group is 6-carboxy-tetramethyl-rhodamine (TAMRA).

7. The reporter system according to claim 1 or 2, wherein said first oligonucleotide is an in-vitro selected or non-natural ribozyme.

8. A method for measuring the catalytic activity of ribozymes which comprises:
   (a) Incubating a reporter system comprised of a first oligonucleotide which is a ribozyme, and a second oligonucleotide which is a substrate for said ribozyme, said second oligonucleotide comprising a label capable of generating a directly measurable signal only when said second oligonucleotide substrate is cleaved by said ribozyme, under conditions at which the ribozyme is catalytically active; and;
   (b) Measuring the amount of cleaved oligonucleotide substrate by measuring said signal.

9. A method for measuring the catalytic activity of ribozymes which comprises the following steps:
   (a) Contacting a reporter system comprised of a first oligonucleotide which is a ribozyyme, and a second oligonucleotide which is a substrate for said ribozyme, said second oligonucleotide comprising a label capable of generating a directly measurable signal only when said second oligonucleotide substrate is cleaved by said ribozyme, with a compound to be tested, under conditions at which the ribozyme is catalytically active; and
   (b) measuring the amount of cleaved oligonucleotide substrate by measuring said signal.

10. The method according to claim 8 or 9, wherein said first oligonucleotide is a hammerhead ribozyyme.

11. The method according to claim 8 or 9, wherein the second oligonucleotide is a double labeled oligonucleotide substrate.

12. The method according to claim 11, wherein the double labeled oligonucleotide substrate contains a fluorophore group and a fluorescence-quenching group and wherein after cleavage of said second oligonucleotide by the ribozyme the fluorescence of the fluorophore is not quenched by the fluorescence-quenching group.

13. The method according to claim 12, wherein the fluorophore group is 6-carboxy-fluorescein (FAM) and the fluorescence-quenching group is 6-carboxy-tetramethyl-rhodamine (TAMRA).

14. The method according to claim 8 or 9, wherein said first oligonucleotide is an in vitro selected or non-natural ribozyme.

* * * * *

SEQUENCE LISTING

<160> NUMBER OF SEQ ID NOS: 9

<210> SEQ ID NO 1
<211> LENGTH: 35
<212> TYPE: RNA
<213> ORGANISM: Unknown
<220> FEATURE:
<223> OTHER INFORMATION: Sequence derived from hammerhead ribozyme

<400> SEQUENCE: 1
ggguccucug augagggccg uuaggccgaa acucc                              35

<210> SEQ ID NO 2
<211> LENGTH: 12
<212> TYPE: RNA
<213> ORGANISM: Unknown
<220> FEATURE:
<223> OTHER INFORMATION: substrate of SEQ ID NO: 1

<400> SEQUENCE: 2
gggagucagg au                                                       12

<210> SEQ ID NO 3
<211> LENGTH: 54
<212> TYPE: DNA
<213> ORGANISM: Artificial Sequence
<220> FEATURE:
<223> OTHER INFORMATION: PCR Primer derived from hammerhead ribozyme -continued

```
<400> SEQUENCE: 3
tctaatacga ctcactatag ggtcctctga tgaggccgtt aggccgaaac tcgt        54

<210> SEQ ID NO 4
<211> LENGTH: 19
<212> TYPE: DNA
<213> ORGANISM: Artificial Sequence
<220> FEATURE:
<223> OTHER INFORMATION: PCR Primer derived from hammerhead ribozyme

<400> SEQUENCE: 4
tctaatacga ctcactata                                               19

<210> SEQ ID NO 5
<211> LENGTH: 19
<212> TYPE: DNA
<213> ORGANISM: Artificial Sequence
<220> FEATURE:
<223> OTHER INFORMATION: PCR Primer derived from hammerhead ribozyme

<400> SEQUENCE: 5
ggcaatccgg ctttgagca                                               19

<210> SEQ ID NO 6
<211> LENGTH: 54
<212> TYPE: DNA
<213> ORGANISM: Unknown
<220> FEATURE:
<223> OTHER INFORMATION: derived from ribozyme variant HHR1mut

<400> SEQUENCE: 6
tctaatacga ctcactatag ggtcctctta ggaggccgtt aggccagaac tcgt        54

<210> SEQ ID NO 7
<211> LENGTH: 19
<212> TYPE: DNA
<213> ORGANISM: Artificial Sequence
<220> FEATURE:
<223> OTHER INFORMATION: PCR Primer derived from ribozyme variant
      HHR1mut

<400> SEQUENCE: 7
tctattacga ctcactata                                               19

<210> SEQ ID NO 8
<211> LENGTH: 19
<212> TYPE: DNA
<213> ORGANISM: Artificial Sequence
<220> FEATURE:
<223> OTHER INFORMATION: PCR Primer derived from ribozyme variant HHR1-
      mut

<400> SEQUENCE: 8
ggcaatccgg tcttgagca                                               19

<210> SEQ ID NO 9
<211> LENGTH: 13
<212> TYPE: RNA
<213> ORGANISM: Unknown
<220> FEATURE:
<223> OTHER INFORMATION: Substrate RNA SL1 purchased from Eurogentec
      (Belgium)

<400> SEQUENCE: 9
acgagucagg auu                                                     13
```